: US 7,696,379 B2
(12) United States Patent
Glatthar et al.

(10) Patent No.: US 7,696,379 B2
(45) Date of Patent: Apr. 13, 2010

(54) ACETYLENE DERIVATIVES

(75) Inventors: Ralf Glatthar, Bad Sackingen (DE); Thomas J. Troxler, Wahlen b. Laufen (DE); Thomas Zoller, Andolsheim (FR); Joachim Nozulak, Heitersheim (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 11/912,626

(22) PCT Filed: Apr. 24, 2006

(86) PCT No.: PCT/EP2006/003766

§ 371 (c)(1),
(2), (4) Date: Oct. 25, 2007

(87) PCT Pub. No.: WO2006/114262

PCT Pub. Date: Nov. 2, 2006

(65) Prior Publication Data

US 2008/0214673 A1 Sep. 4, 2008

(30) Foreign Application Priority Data

Apr. 25, 2005 (GB) ................... 0508319.1

(51) Int. Cl.
C07C 231/00 (2006.01)
C07D 263/02 (2006.01)
C07D 261/02 (2006.01)
C07D 249/08 (2006.01)
C07D 233/00 (2006.01)
C07C 237/00 (2006.01)
A61K 31/33 (2006.01)
A61K 31/16 (2006.01)

(52) U.S. Cl. ................ 564/138; 549/483; 548/215; 548/240; 548/262.2; 548/300.1; 544/224; 514/183; 514/613

(58) Field of Classification Search ............. 564/138; 544/224; 548/215, 240, 262.2, 300.1; 549/483; 514/183, 613
See application file for complete search history.

(56) References Cited

U.S. PATENT DOCUMENTS

| | | | |
|---|---|---|---|
| 3,991,064 | A | 11/1976 | Brown et al. |
| 5,521,297 | A * | 5/1996 | Daggett et al. ............ 536/23.5 |
| 5,576,336 | A | 11/1996 | Baker et al. |
| 5,665,722 | A | 9/1997 | Kulagowski et al. |
| 5,688,798 | A | 11/1997 | Godel et al. |
| 5,714,498 | A | 2/1998 | Kulagowski et al. |
| 5,830,901 | A | 11/1998 | Curtis et al. |
| 2003/0149049 | A1 | 8/2003 | Arkin et al. |
| 2004/0077667 | A1 | 4/2004 | Matsuoka et al. |
| 2004/0167224 | A1 | 8/2004 | Ozaki et al. |
| 2005/0065191 | A1 * | 3/2005 | Gasparini et al. ............ 514/357 |
| 2008/0188490 | A1 | 8/2008 | Glatthar et al. |
| 2008/0194551 | A1 | 8/2008 | Glatthar et al. |
| 2008/0269250 | A1 | 10/2008 | Glatthar et al. |

FOREIGN PATENT DOCUMENTS

| | | |
|---|---|---|
| EP | 1 484 327 A1 | 12/2004 |
| FR | 2 761 069 A1 | 9/1998 |
| WO | WO 94/20459 | 9/1994 |
| WO | WO 94/21615 A1 | 9/1994 |
| WO | WO 94/21627 A1 | 9/1994 |
| WO | WO 95/29911 A1 | 11/1995 |
| WO | WO 96/05200 A1 | 2/1996 |
| WO | WO 97/13759 A1 | 4/1997 |
| WO | WO 97/28141 A1 | 8/1997 |
| WO | WO 00/25768 A1 | 5/2000 |
| WO | WO 00/59503 | 10/2000 |
| WO | WO 01/30330 A2 | 5/2001 |
| WO | WO 01/54498 A1 | 8/2001 |
| WO | WO 01/58891 A2 | 8/2001 |
| WO | WO 2002/46166 A1 | 6/2002 |
| WO | WO 02/062323 A2 | 8/2002 |
| WO | WO 03/037338 A2 | 5/2003 |
| WO | WO 03/047581 A1 | 6/2003 |

(Continued)

OTHER PUBLICATIONS

Peter C. Chua et al., "Cyclohexenyl —and dehydropiperidinyl-alkynul pyridines as potent metabotropic glutamate subtype 5 (mG1u5) receptor antagonists", Bioorganic & Medicinal Chemistry Letters, Oxford, GB, vol. 15, No. 20, pp. 4589-4593, Oct. 15, 2005.

(Continued)

Primary Examiner—Sikarl A Witherspoon
(74) Attorney, Agent, or Firm—Paul D. Strain; Fanelli, Strain & Haag, PLLC

(57) ABSTRACT

The invention provides compounds of formula (I)

(I)

wherein
$R^1$ represents hydrogen or alkyl;
$R^2$ represents an unsubstituted or substituted heterocycle or
$R^2$ represents an unsubstituted or substituted aryl;
$R^3$ represents alkyl or halogen;
X represents a single bond or an alkandiyl-group, optionally interrupted by one or more oxygen atoms or carbonyl groups or carbonyloxy groups in free base or acid addition salt form, processes for their preparation and their use as pharmaceuticals.

14 Claims, No Drawings

FOREIGN PATENT DOCUMENTS

| WO | WO 03/084948 A1 | 10/2003 |
| WO | WO 04/011430 A1 | 2/2004 |
| WO | WO 2004/031148 A1 | 4/2004 |
| WO | WO 2004/038374 A2 | 5/2004 |
| WO | WO 2005/044797 A1 | 5/2005 |
| WO | WO 2005/118587 A1 | 12/2005 |
| WO | WO 2006/089700 A1 | 8/2006 |
| WO | WO 2006/114260 A1 | 11/2006 |
| WO | WO 2006/114264 A1 | 11/2006 |
| WO | WO 2007/006530 A1 | 1/2007 |

OTHER PUBLICATIONS

N. J. Harper, et al., "Ethynyl and Styryl Compounds of the Prodine Type.", J. Med. Pharm. Chem., vol. 4, No. 2, 1961, pp. 297-316.

Jorand-Lebrun et al., Use of Triphosgene for Direct Preparation of Carbamoyl Chlorides from Tertiary Benzylamines, Synthetic Communications., Database Beilstein, XP002384771, Database accession No. 7927499, abstract, vol. 28, No. 7, 1998, pp. 1189-1196.

K. Eichinger, et al., "Ethinylepoxide als Synthone fur 1,3-Diketone und Furane," J. Chem. Res. Miniprint, vol. 7, 1983, pp. 1625-1649.

Cecil Textbook of Medicine, $20^{th}$ edition, 1996, vol. 2, pp. 2050-2057.

Cecil Textbook of Medicine, $20^{th}$ edition, 1996, vol. 2, pp. 1992-1996.

FDA mulls drug to slow late-stage Alzheimer's [online], [retrieved on Sep. 23, 2003], Retrieved from the internet, URL; http://www.cnn.com/2003HEALTH/conditions/09/24/alzheimers.drug.ap/indexhtml>.

Harald Huebner, et al.,"Conjugated enynes as nonaromatic catechol bioisosteres: Synthesis, binding experiments, and computational studies of novel dopamine receptor agonists recognizing preferentially the D3 subtype", Journal of Medicinal Chemistry, vol. 43, No. 4, Feb. 24, 2000, pp. 756- 762.

Ralf Glatthar et al., Office Action, U.S. Appl. No. 11/912,624, Dec. 10, 2008.

Ralf Glatthar et al., Office Action, U.S. Appl. No. 11/912,622, Dec. 11, 2008.

Ralf Glatthar et al., U.S. PTO Office Action, U.S. Appl. No. 11/912,624, Sep. 25, 2009, 8 pages.

Ralf Glatthar et al., U.S. PTO Office Action, U.S. Appl. No. 11/912,622, Sep. 14, 2009, 12 pages.

* cited by examiner

ACETYLENE DERIVATIVES

This application is the National Stage of Application No. PCT/EP2006/003766, filed on Apr. 24, 2006, which claims benefit under 35 U.S.C. § 119(e) of Great Britain Application No. 0508319.1, filed Apr. 25, 2005. The contents of both are incorporated herein by reference in their entirety.

The present invention relates to novel acetylene derivatives, their preparation, their use as pharmaceuticals and pharmaceutical compositions containing them.

More particularly the invention provides a compound of formula (I)

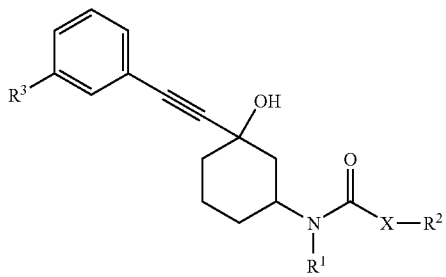

(I)

wherein
$R^1$ represents hydrogen or alkyl;
$R^2$ represents an unsubstituted or substituted heterocycle or
$R^2$ represents an unsubstituted or substituted aryl;
$R^3$ represents alkyl or halogen;
X represents a single bond or an alkandiyl-group, optionally interrupted by one or more oxygen atoms or carbonyl groups or carbonyloxy groups in free base or acid addition salt form.

In the present specification, the following definitions shall apply if no specific other definition is given:

"Alkyl" represents a straight-chain or branched-chain alkyl group, preferably represents a straight-chain or branched-chain $C_{1-12}$alkyl, particularly preferably represents a straight-chain or branched-chain $C_{1-6}$-alkyl; for example, methyl, ethyl, n- or iso-propyl, n-, iso-, sec- or tert-butyl, n-pentyl, n-hexyl, n-heptyl, n-octyl, n-nonyl, n-decyl, n-undecyl, n-dodecyl, with particular preference given to methyl, ethyl, n-propyl and iso-propyl.

"Alkandiyl" represents a straight-chain or branched-chain alkandiyl group bound by two different Carbon atoms to the molecule, it preferably represents a straight-chain or branched-chain $C_{1-12}$ alkandiyl, particularly preferably represents a straight-chain or branched-chain $C_{1-6}$ alkandiyl; for example, methandiyl (—$CH_2$—), 1,2-ethanediyl (—$CH_2$—$CH_2$—), 1,1-ethanediyl ((—$CH(CH_3)$—), 1,1-, 1,2-, 1,3-propanediyl and 1,1-, 1,2-, 1,3-, 1,4-butanediyl, with particular preference given to methandiyl, 1,1-ethanediyl, 1,2-ethanediyl, 1,3-propanediyl, 1,4-butanediyl.

Each alkyl part of "alkoxy", "alkoxyalkyl", "alkoxycarbonyl", "alkoxycarbonylalkyl" and "halogenalkyl" shall have the same meaning as described in the above-mentioned definition of "alkyl".

"Alkenyl" represents a straight-chain or branched-chain alkenyl group, preferably $C_{2-6}$alkenyl, for example, vinyl, allyl, 1-propenyl, isopropenyl, 2-butenyl, 2-pentenyl, 2-hexenyl, etc. and preferably represents $C_{2-4}$ alkenyl.

"Alkendiyl" represents a straight-chain or branched-chain alkendiyl group bound by two different Carbon atoms to the molecule, it preferably represents a straight-chain or branched-chain $C_{2-6}$ alkandiyl; for example, —CH=CH—, —CH=C(CH₃)—, —CH=CH—CH₂—, —C(CH₃)=CH—CH₂—, —CH=C(CH₃)—CH₂—, —CH=CH—C(CH₃)H—, —CH=CH—CH=CH—, —C(CH₃)=CH—CH=CH—, —CH=C(CH₃)—CH=CH—, with particular preference given to —CH=CH—CH₂—, —CH=CH—CH=CH—.

"Alkynyl" represents a straight-chain or branched-chain alkynyl group, preferably $C_{2-6}$alkynyl, for example, ethenyl, propargyl, 1-propynyl, isopropenyl, 1-(2- or 3) butynyl, 1-(2- or 3) pentenyl, 1-(2- or 3) hexenyl, etc., preferably represents $C_{2-4}$alkynyl and particularly preferably represents ethynyl.

"Aryl" represents an aromatic hydrocarbon group, preferably a $C_{6-10}$ aromatic hydrocarbon group; for example phenyl, naphthyl, especially phenyl.

"Aralkyl" denotes an "Aryl" bound to an "Alkyl" (both as defined above) an represents, for example benzyl, α-methylbenzyl, 2-phenylethyl, α,α-dimethylbenzyl, especially benzyl.

"Heterocycle" represents a saturated, partly saturated or aromatic ring system containing at least one hetero atom. Preferably, heterocycles consist of 3 to 11 ring atoms of which 1-3 ring atoms are hetero atoms. Heterocycles may be present as a single ring system or as bicyclic or tricyclic ring systems; preferably as single ring system or as benz-annelated ring system. Bicyclic or tricyclic ring systems may be formed by annelation of two or more rings, by a bridging atom, e.g. Oxygen, sulfur, nitrogen or by a bridging group, e.g. alkandediyl or alkenediyl. A Heterocycle may be substituted by one or more substituents selected from the group consisting of Oxo (=O), Halogen, Nitro, Cyano, Alkyl, Alkandiyl, Alkenediyl, Alkoxy, Alkoxyalkyl, Alkoxycarbonyl, Alkoxycarbonylalkyl, Halogenalkyl, Aryl, Aryloxy, Arylalkyl. Examples of heterocyclic moieties are: pyrrole, pyrroline, pyrrolidine, pyrazole, pyrazoline, pyrazolidine, imidazole, imidazoline, imidazolidine, triazole, triazoline, triazolidine, tetrazole, furane, dihydrofurane, tetrahydrofurane, furazane (oxadiazole), dioxolane, thiophene, dihydrothiophene, tetrahydrothiophene, oxazole, oxazoline, oxazolidine, isoxazole, isoxazoline, isoxazolidine, thiazole, thiazoline, thiazolidine, isothiazole, istothiazoline, isothiazolidine, thiadiazole, thiadiazoline, thiadiazolidine, pyridine, piperidine, pyridazine, pyrazine, piperazine, triazine, pyrane, tetrahydropyrane, thiopyrane, tetrahydrothiopyrane, oxazine, thiazine, dioxine, morpholine, purine, pterine, and the corresponding benz-annelated heterocycles, e.g. indole, isoindole, cumarine, cumaronecinoline, isochinoline, cinnoline and the like.

"Hetero atoms" are atoms other than Carbon and Hydrogen, preferably Nitrogen (N), Oxygen (O) or Sulfur (S).

"Halogen" represents Fluoro, Chloro, Bromo or Iodo, preferably represents Fluoro, Chloro or Bromo and particularly preferably represents Chloro.

Compounds of formula (I) exist in free or acid addition salt form. In this specification, unless otherwise indicated, language such as "compounds of formula (I)" is to be understood as embracing the compounds in any form, for example free base or acid addition salt form. Salts which are unsuitable for pharmaceutical uses but which can be employed, for example, for the isolation or purification of free compounds of formula (I), such as picrates or perchlorates, are also included. For therapeutic use, only pharmaceutically acceptable salts or free compounds are employed (where applicable in the form of pharmaceutical preparations), and are therefore preferred.

On account of the asymmetrical carbon atom(s) that may be present in the compounds of formula (I) and their salts, the compounds may exist in optically active form or in form of mixtures of optical isomers, e.g. in form of racemic mixtures or diastereomeric mixtures. All optical isomers and their mixtures, including the racemic mixtures, are part of the present invention. The trans-Isomers of the compounds of formula (I) are preferred.

Preferred substituents, preferred ranges of numerical values or preferred ranges of the radicals present in the formula (I), (I') and the corresponding intermediate compounds are defined below.

$R^1$ preferably represents hydrogen or $C_{1-4}$ alkyl.
$R^1$ particularly preferably represents hydrogen.
$R^3$ preferably represents Fluoro, Chloro, $C_{1-4}$ alkyl.
$R^3$ particularly preferably represents chloro or methyl.
$R^2$ preferably represents an unsubstituted or substituted heterocycle having 3-11 ring atoms and 1-4 hetero atoms; the hetero atoms being selected from the group consisting of N, O, S, the substituents being selected from the group consisting of Oxo (=O), Hydroxy, Halogen, Amino, Nitro, Cyano, $C_{1-4}$ Alkyl, $C_{1-4}$ Alkoxy, $C_{1-4}$ Alkoxyalkyl, $C_{1-4}$ Alkoxycarbonyl, $C_{1-4}$ Alkoxycarbonylalkyl, $C_{1-4}$ Halogenalkyl, $C_{6-10}$ Aryl, Halogen-$C_{6-10}$ Aryl, $C_{6-10}$ Aryloxy, $C_{6-10}$-Aryl-$C_{1-4}$ alkyl.
$R^2$ further preferably represents phenyl or substituted phenyl, the substituents being selected from the group consisting of Hydroxy, Amino, Halogen, Nitro, Cyano, $C_{1-4}$ Alkyl, $C_{1-4}$ Alkoxy, $C_{1-4}$ Alkoxyalkyl, $C_{1-4}$ Alkoxycarbonyl, $C_{1-4}$ Alkoxycarbonylalkyl, $C_{1-4}$ Halogenalkyl, $C_{6-10}$ Aryl, Halogen-$C_{6-10}$ Aryl, $C_{6-10}$ Aryloxy, $C_{6-10}$-Aryl-$C_{1-4}$ alkyl.
$R^2$ particularly preferably represents an unsubstituted, a single or twofold substituted heterocycle having 5-9 ring atoms and 1-3 hetero atoms; the hetero atoms being selected from the group consisting of N, O; the substituents being selected from the group consisting of Halogen, $C_{1-4}$ Alkyl.
$R^2$ particularly preferably represents an unsubstituted, a single or twofold substituted phenyl, the substituents being selected from the group consisting of fluoro, chloro, hydroxy, methyl, methoxy, methoxycarbonyl, trifluormethoxy, amino, dimethylamino, methylthio, methylsulfonyl.
$R^2$ very particularly preferably represents an unsubstituted, a single or twofold substituted heterocycle selected from the group consisting of

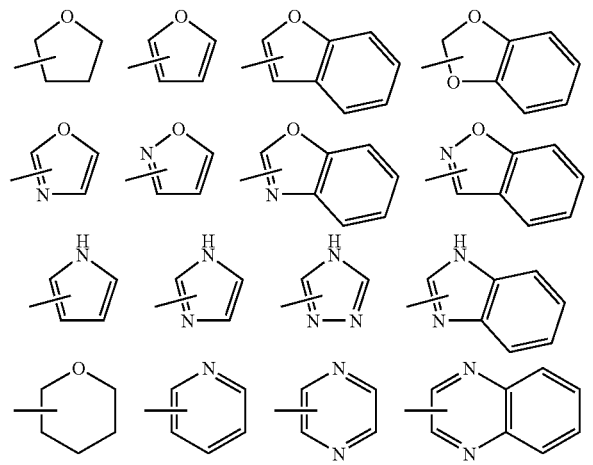

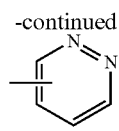

and the substituents selected from the group consisting of fluoro, chloro, methyl, methylthio, amino.

$R^2$ further very particularly preferably represents a substituent selected from the group consisting of

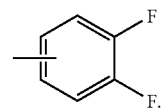

X preferably represents $C_{1-6}$ alkandiyl, $C_{1-6}$ alkandiyl with an oxygen group at the end or $C_{1-6}$ alkandiyl with an carbonyl group at the end, $C_{1-6}$ alkandiyl with an carbonyloxy group at the end.

X particular preferably represents, methandiyl (—$CH_2$—), 1,2-ethanediyl (—$CH_2$—$CH_2$—), 1,1-ethanediyl ((—CH($CH_3$)—), methandiyloxy (—O—$CH_2$—), 1,2-ethanediyloxy (—O—$CH_2$—$CH_2$—), 1,1-ethanediyloxy ((—O—CH($CH_3$)—), methandiylcarbonyl (—CO—$CH_2$—), 1,2-ethanediylcarbonyl (—CO—$CH_2$—$CH_2$—), 1,1-ethanediylcarbonyl ((—CO—CH($CH_3$)—), methandiylcarbonyloxy (—C(O)O—$CH_2$—), 1,2-ethanediylcarbonyloxy (—C(O)O—$CH_2$—$CH_2$—), 1,1-ethanediylcarbonyloxy ((—C(O)O—CH($CH_3$)—). The functional groups as defined for X are preferably bound to the group $R^2$.

In a further embodiment, the invention provides a compound of formula (I')

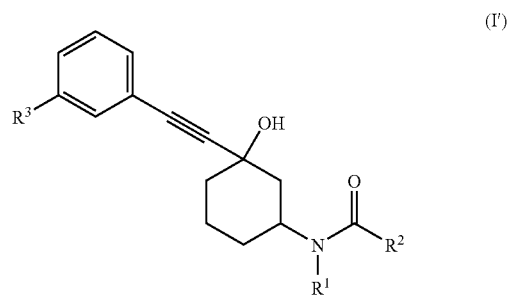

wherein
$R^1$ represents hydrogen or alkyl;
$R^2$ represents an unsubstituted or substituted heterocycle or
$R^2$ represents an unsubstituted or substituted aryl;
$R^3$ represents alkyl or halogen;

in free base or acid addition salt form.

The abovementioned general or preferred radical definitions apply both to the end products of the formula (I) and also, correspondingly, to the starting materials or intermediates required in each case for the preparation. These radical definitions can be combined with one another at will, i.e. including combinations between the given preferred ranges. Further, individual definitions may not apply.

Preference according to the invention is given to compounds of the formula (I) which contain a combination of the meanings mentioned above as being preferred.

Particular preference according to the invention is given to compounds of the formula (I) which contain a combination of the meanings listed above as being particularly preferred.

Very particular preference according to the invention is given to the compounds of the formula (I) which contain a combination of the meanings listed above as being very particularly preferred.

Preferred are compounds of formula (I) wherein $R^2$ represents an unsubstituted or substituted heterocycle.

In a further embodiment, the invention provides a compound of formula (I″)

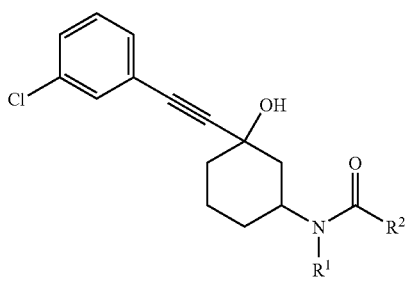

(I″)

wherein $R^1$ and $R^2$ are as defined above.

In a further embodiment, the invention provides a compound of formula (I″) as defined above, wherein $R^2$ is as defined above and $R^1$ represents hydrogen.

In a further aspect, the invention provides a process for the production of the compounds of formula I and their salts, which comprises the step of reacting a compound of formula (II)

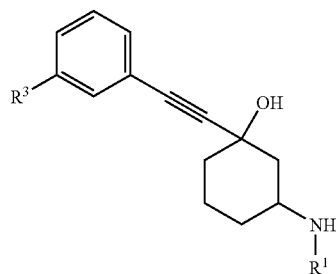

(II)

wherein $R^1$ and $R^3$ are as defined above, with a compound of formula (III)

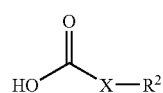

(III)

wherein X and $R^2$ are as defined above and recovering the resulting compound of formula (I) in free base or acid addition salt form.

The reaction of process a) can be effected according to conventional methods, e.g. as described in Example 1.

Optionally, the reaction is carried out under basic conditions, e.g. by using an amine as a suitable base, for example triethylamine.

Starting materials of formula (III) are known or obtainable by known methods.

The starting materials of formula (II) are obtainable by cleavage of an carbamic acid of formula (IV)

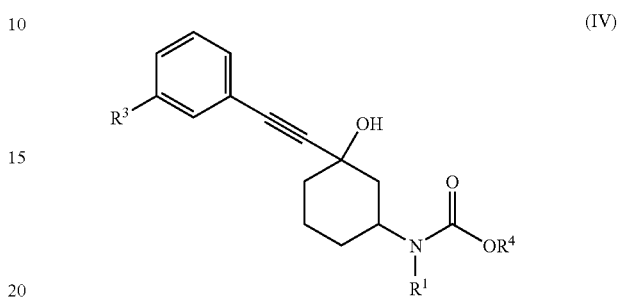

(IV)

wherein $R^1$ and $R^3$ are as defined above and $R^4$ represents $C_1$-$C_4$alkyl, preferably tert.butyl or methyl, under acid conditions, e.g. by using HCl in an organic solvent, such as dioxane.

Compounds of formula (IV) are known, e.g. from WO 03/047581.

A so obtained compound of formula (I) can be converted into another compound of formula (I) according to conventional methods.

The following considerations apply to the individual reaction steps described above:

a) One or more functional groups, for example carboxy, hydroxy, amino, or mercapto, may need to be protected in the starting materials by protecting groups. The protecting groups employed may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned hereinabove and hereinafter. The protection of such functional groups by such protecting groups, the protecting groups themselves, and their removal reactions are described for example in standard reference works, such as J. F. W. McOmie, "Protective Groups in Organic Chemistry", Plenum Press, London and New York 1973, in T. W. Greene, "Protective Groups in Organic Synthesis", Wiley, New York 1981, in "The Peptides"; Volume 3 (editors: E. Gross and J. Meienhofer), Academic Press, London and New York 1981, in "Methoden der organischen Chemie" (Methods of organic chemistry), Houben Weyl, 4th edition, Volume 15/I, Georg Thieme Verlag, Stuttgart 1974, in H.-D. Jakubke and H. Jescheit, "Aminosäuren, Peptide, Proteine" (Amino acids, peptides, proteins), Verlag Chemie, Weinheim, Deerfield Beach, and Basel 1982, and in Jochen Lehmann, "Chemie der Kohlenhydrate: Monosaccharide und Derivate" (Chemistry of carbohydrates: monosaccharides and derivatives), Georg Thieme Verlag, Stuttgart 1974.

b) Acid addition salts may be produced from the free bases in known manner, and vice-versa. Compounds of formula (I) in optically pure form can be obtained from the corresponding racemates according to well-known procedures, e.g. HPLC with chiral matrix. Alternatively, optically pure starting materials can be used.

c) Stereoisomeric mixtures, e.g. mixtures of diastereomers, can be separated into their corresponding isomers in a manner known per se by means of suitable separation methods. Diastereomeric mixtures for example may be separated into their individual diastereomers by means of fractionated crystallization, chromatography, solvent distribution, and similar procedures. This separation may take place either at the level of a starting compound or in a compound of formula I itself. Enantiomers may be separated through the formation of diastereomeric salts, for example by salt formation with an enantiomer-pure chiral acid, or by means of chromatography, for example by HPLC, using chromatographic substrates with chiral ligands.

d) Suitable diluents for carrying out the above-described are especially inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile propionitrile or butyronitrile; amides, such as N,N-dimethylformamide, N,N-dimethylacetamide, N-methyl-formanilide, N-methylpyrrolidone or hexamethylphosphoric triamide; esters, such as methyl acetate or ethyl acetate, sulphoxides, such as dimethyl sulphoxide, alcohols, such as methanol, ethanol, n- or i-propanol, ethylene glycol monomethyl ether, ethylene glycol monoethyl ether, diethyelene glycol monomethyl ether, diethylene glycol monoethyl ether. Further, mixtures of diluents may be employed. Depending on the starting materials, reaction conditions and auxiliaries, water or diluents containing water may be suitable. It is also possible to use one a starting material as diluent simultaneously.

e) Reaction temperatures can be varied within a relatively wide range. In general, the processes are carried out at temperatures between 0° C. and 150° C., preferably between 10° C. and 120° C. Deprotonation reactions can be varied within a relatively wide range. In general, the processes are carried out at temperatures between −150° C. and +50° C., preferably between −75° C. and 0° C.

f) The reactions are generally carried out under atmospheric pressure. However, it is also possible to carry out the processes according to the invention under elevated or reduced pressure—in general between 0.1 bar and 10 bar.

g) Starting materials are generally employed in approximately equimolar amounts. However, it is also possible to use a relatively large excess of one of the components. The reaction is generally carried out in a suitable diluent in the presence of a reaction auxiliary, and the reaction mixture is generally stirred at the required temperature for a number of hours.

h) Work-up is carried out by customary methods (cf. the Preparation Examples).

Compounds of formula (I) and their pharmaceutically acceptable acid addition salts, hereinafter referred to as agents of the invention, exhibit valuable pharmacological properties and are therefore useful as pharmaceuticals.

In particular, the agents of the invention exhibit a marked and selective modulating, especially antagonistic, action at human metabotropic glutamate receptors (mGluRs). This can be determined in vitro for example at recombinant human metabotropic glutamate receptors, especially PLC-coupled subtypes thereof such as mGluR5, using different procedures like, for example, measurement of the inhibition of the agonist induced elevation of intracellular $Ca^{2+}$ concentration in accordance with L. P. Daggett et al., Neuropharm. Vol. 34, pages 871-886 (1995), P. J. Flor et al., J. Neurochem. Vol. 67, pages 58-63 (1996) or by determination to what extent the agonist induced elevation of the inositol phosphate turnover is inhibited as described by T. Knoepfel et al., Eur. J. Pharmacol. Vol. 288, pages 389-392 (1994), L. P. Daggett et al., Neuropharm. Vol. 67, pages 58-63 (1996) and references cited therein. Isolation and expression of human mGluR subtypes are described in U.S. Pat. No. 5,521,297. Selected agents of the invention show IC50 values for the inhibition of the agonist (e.g. glutamate or quisqualate) induced elevation of intracellular Ca2+ concentration or the agonist (e.g. glutamate or quisqualate) induced inositol phosphate turnover, measured in recombinant cells expressing hmGluR5a of about 1 nM to about 50 μM.

The agents of the invention are therefore useful in the prevention, treatment or delay of progression of disorders associated with irregularities of the glutamatergic signal transmission, of the gastro-intestinal and urinary tract and of nervous system disorders mediated full or in part by mGluR5.

Disorders associated with irregularities of the glutamatergic signal transmission are for example epilepsy, cerebral ischemias, especially acute ischemias, ischemic diseases of the eye, muscle spasms such as local or general spasticity, skin disorders, obesity disorders and, in particular, convulsions or pain.

Disorders of the gastro-intestinal tract include post-operative ileus, functional gastro-intestinal disorders (FGID) as for example functional dyspepsia (FD), gastro-esophageal reflux disease (GERD), irritable bowel syndrome (IBS), functional bloating, functional diarrhea, chronic constipation, functional disturbancies of the biliary tract as well as other conditions according to Gut 1999; Vol. 45 Suppl II.

Disorders of the Urinary Tract comprise conditions associated with pain and/or discomfort of the urinary tract and overactive bladder (OAB).

Nervous system disorders mediated full or in part by mGluR5 are for example acute, traumatic and chronic degenerative processes of the nervous system, such as Parkinson's disease, senile dementia, Alzheimer's disease, Huntington's chorea, amyotrophic lateral sclerosis, multiple sclerosis and fragile X syndrome, psychiatric diseases such as schizophrenia and anxiety, depression, pain, itch and drug abuse. Anxiety related disorders includes panic disorders, social anxiety, obsessive compulsive disorders (OCD), post traumatic stress disorders (ATSD), generalized anxiety disorders (GAD), phobias.

The usefulness of the agents of the invention in the prevention, treatment or delay of progression of the above-mentioned disorders can be confirmed in a range of standard tests including those indicated below:

Activity of the agents of the invention in anxiety can be demonstrated in standard models such as the stress-induced hyperthermia in mice [cf. A. Lecci et al., Psychopharmacol. 101, 255-261]. At doses of about 0.1 to about 30 mg/kg p.o., selected agents of the invention reverse the stress-induced hyperthermia.

At doses of about 4 to about 50 mg/kg p.o., selected agents of the invention show reversal of Freund complete adjuvant (FCA) induced hyperalgesia [cf. J. Donnerer et al., Neuroscience 49, 693-698 (1992) and C. J. Woolf, Neuroscience 62, 327-331 (1994)].

For all the above mentioned indications, the appropriate dosage will of course vary depending upon, for example, the compound employed, the host, the mode of administration and the nature and severity of the condition being treated. However, in general, satisfactory results in animals are indicated to be obtained at a daily dosage of from about 0.5 to about 100 mg/kg animal body weight. In larger mammals, for example humans, an indicated daily dosage is in the range from about 5 to 1500 mg, preferably about 10 to about 1000 mg of the compound conveniently administered in divided doses up to 4 times a day or in sustained release form.

In accordance with the foregoing, the present invention also provides an agent of the invention for use as a pharmaceutical, e.g. in the prevention, treatment or delay of progression of disorders associated with irregularities of the glutamatergic signal transmission, and of nervous system disorders mediated full or in part by mGluR5.

The invention also provides the use of an agent of the invention, in the prevention, treatment or delay of progression of disorders associated with irregularities of the glutamatergic signal transmission, of the gastro-intestinal and urinary tract and of nervous system disorders mediated full or in part by mGluR5.

Furthermore the invention provides the use of an agent of the invention for the manufacture of a pharmaceutical composition designed for the prevention, treatment or delay of progression of disorders associated with irregularities of the glutamatergic signal transmission, and of nervous system disorders mediated full or in part by mGluR5.

In a further aspect the invention relates to a method of treating disorders mediated full or in part by mGluR5, which method comprises administering to a warm-blooded organism in need of such treatment a therapeutically effective amount of an agent of the invention.

Moreover the invention relates to a pharmaceutical composition comprising an agent of the invention in association with one or more pharmaceutical carrier or one or more pharmaceutically acceptable diluent.

The pharmaceutical compositions according to the invention are compositions for enteral, such as nasal, rectal or oral, or parenteral, such as intramuscular or intravenous, administration to warm-blooded animals (human beings and animals) that comprise an effective dose of the pharmacological active ingredient alone or together with a significant amount of a pharmaceutically acceptable carrier. The dose of the active ingredient depends on the species of warm-blooded animal, body weight, age and individual condition, individual pharmacokinetic data, the disease to be treated and the mode of administration.

The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, dragées, tablets or capsules.

The pharmaceutical compositions of the present invention are prepared in a manner known per se, for example by means of conventional dissolving, lyophilizing, mixing, granulating or confectioning processes.

The preferred agents of the invention include the Furan-3-carboxylic acid [(1R,3R)-3-(3-chloro-phenylethynyl)-3-hydroxy-cyclohexyl]-amide free base or pharmaceutically acceptable acid addition salt form.

Furan-3-carboxylic acid [(1R,3R-3-(3-chloro-phenylethynyl)-3-hydroxy-cyclohexyl]-amide inhibits the quinqualate-induced inositol phosphate turnover in hmGluR5 expressing cells with an $IC_{50}$ concentration of 28 nM.

With Furan-3-carboxylic acid [(1R,3R)-3-(3-chloro-phenylethynyl)-3-hydroxy-cyclohexyl]-amide, a stress-induced hyperthermia of 0.82+/−0.1° C. was reduced to 0.37+/−0.10° C. at 3 mg/kg p.o., to 0.02+/−0.08° C. at 10 mg/kg p.o. and to −0.49+/−0.12° C. at 30 mg/kg p.o. ($p<0.01$; $p<0.001$; $p<0.001$ respectively).

Further, properly isotope-labeled agents of the invention exhibit valuable properties as histopathological labeling agents, imaging agents and/or biomarkers, hereinafter "markers", for the selective labeling of the metabotropic glutamate receptor subtype 5 (mGlu5 receptor). More particularly the agents of the invention are useful as markers for labeling the central and peripheral mGlu5 receptors in vitro or in vivo. In particular, compounds of the invention which are properly isotopically labeled are useful as PET markers. Such PET markers are labeled with one or more atoms selected from the group consisting of $^{11}C$, $^{13}N$, $^{15}O$, $^{18}F$.

The agents of the invention are therefore useful, for instance, for determining the levels of receptor occupancy of a drug acting at the mGlu5 receptor, or diagnostic purposes for diseases resulting from an imbalance or dysfunction of mGlu5 receptors, and for monitoring the effectiveness of pharmacotherapies of such diseases.

In accordance with the above, the present invention provides an agent of the invention for use as a marker for neuroimaging.

In a further aspect, the present invention provides a composition for labeling brain and peripheral nervous system structures involving mGlu5 receptors in vivo and in vitro comprising an agent of the invention.

In still a further aspect, the present invention provides a method for labeling brain and peripheral nervous system structures involving mGlu5 receptors in vitro or in vivo, which comprises contacting brain tissue with an agent of the invention.

The method of the invention may comprise a further step aimed at determining whether the agent of the invention labeled the target structure. Said further step may be effected by observing the target structure using positron emission tomography (PET) or single photon emission computed tomography (SPECT), or any device allowing detection of radioactive radiations.

The following non-limiting Examples illustrate the invention. A list of Abbreviations used is given below.

BOC tert-butoxycarbonyl
n-BuLi n-butyl lithium
DCM dichloromethane
DMF N,N'-dimethylformamide
EDC 1-ethyl-3-[3-(dimethylamino)propyl]-carbodiimide hydrochloride
EtOAc ethylacetate
h hours
HCl hydrochloric acid
HOBt hydroxybenzotriazole
HPLC high pressure liquid chromatography
min minutes
Mp melting point
MS mass spectroscopy
MTBE methyl-tert.-butylether
Rf retention factor (Thin Layer Chromatography)
Rt retention time (LC/MS)

rt room temperature
TFA trifluoroacetic acid
THF tetrahydrofuran

EXAMPLE 1

Furan-3-carboxylic acid [(1R,3R)-3-(3-chloro-phenylethynyl)-3-hydroxy-cyclohexyl]-amide (+)-(1R,3R)-3-Amino-1-(3-chloro-phenylethynyl)-cyclohexanol (115 mg, 0.46 mmol) was dissolved in DMF (5 ml) and treated with furan-3-carboxylic acid ((63 mg, 0.55 mmol) and EDC (108 mg, 0.55 mmol). After stirring for 1.5 h at room temperature, Et3N (0.55 mmol) was added and stirring continued for 18 h. A second batch of EDC (108 mg, 0.55 mmol) was added and stirring continued for 6 h. EtOAc was added and the mixture washed with aqueous sodium bicarbonate and brine. Drying of the organic phase with Na2SO4, filtration and evaporation afforded a crude product (263 mg) which was purified by chromatography on silica gel to afford the title compound as a white solid (105 mg, 66%). MS (LC/MS): 344.2 [M+H]; $[\alpha]_D$=+95.6° (c=0.5, MeOH).

The starting material was prepared as described hereafter:

i) (3-Oxo-cyclohexyl)-carbamic acid tert-butyl ester

A solution of 2-cyclohexen-1-on (14 ml, 150 mmol) and t-butylcarbamate (17 g, 145.11 mmol) in DCM (30 ml) was treated with bismuth nitrate pentahydrate (14 g, 28.8 mmol) and stirred at room temperature for 21 h. Dilution with further DCM, filtration over hyflo, washing of the filtrate with sodium bicarbonate solution and brine, drying of the organic phase with Na2SO4, filtration and evaporation of the solvent afforded 22.1 g of the crude product. Chromatography on silica gel (EtOAc/cyclohexanol 3:7), followed by crystallization from the same solvent system afforded (3-oxo-cyclohexyl)-carbamic acid tert-butyl ester (14.43 g, 47%).

ii) rac-[(trans)-3-(3-Chloro-phenylethynyl)-3-hydroxy-cyclohexyl]-carbamic acid tert-butyl ester 1-Chloro-3-ethynyl-benzene (9.0 ml, 71 mmol) was dissolved in THF (250 ml) and cooled to −20°. A solution of n-BuLi in hexanes (44 ml, 1.6 M, 70 mmol) was added dropwise and the mixture stirred at −20° for 2 h. After cooling to −60°, a solution of (3-oxo-cyclohexyl)-carbamic acid tert-butyl ester (15.15 g, 71 mmol) in THF (100 ml) was added slowly. The mixture was allowed to reach room temperature and then stirred for 16 h. Dilution of the mixture with EtOAc, washing with sodium bicarbonate solution and brine, drying of the organic phase with Na2SO4, filtration and evaporation of the solvent afforded a crude product as a mixture of cis and trans isomers. Careful chromatography on silica gel with EtOAc/cyclohexane 4:6 afforded first the desired rac-(trans) isomer ('trans' for —OH and —NH, 2.48 g, 10%), followed by the rac-(cis) isomer ('cis' for —OH and —NH, 8 g).

iii) (+)-[(1R,3R)-3-(3-Chloro-phenylethynyl)-3-hydroxy-cyclohexyl]-carbamic acid tert-butyl ester rac-[(1R,3R)-3-(3-Chloro-phenylethynyl)-3-hydroxy-cyclohexyl]-carbamic acid tert-butyl ester (2.26 g) was separated into its enantiomers via HPLC using Chiralcel OD as stationary phase and hexanes/EtOH as eluent. 1.1 g of each enantiomer was isolated. $[\alpha]_D$=+98.5° (c=0.5, MeOH) and −94.3° (c=0.6, MeOH), respectively.

iv) (+)-(1R,3R)-3-Amino-1-(3-chloro-phenylethynyl)-cyclohexanol (+)-[(1R,3R)-3-(3-Chloro-phenylethynyl)-3-hydroxy-cyclohexyl]-carbamic acid tert-butyl ester (1.03 g, 2.94 mmol) was dissolved in EtOAc (15 ml) and cooled to 0°. A solution of HCl in dioxane (11 ml, 4M, 44 mmol) was added dropwise and the mixture stirred for 4.5 h at 0°. The clear solution was poured on an aqueous solution of sodium bicarbonate and the phases separated. Extraction of the aqueous phase with EtOAc, washing of the combined organic phases with brine and evaporation afforded a crude product that was purified by chromatography on silica gel. 740 mg (100%) of the optically pure primary amine (+)-(1R,3R)-3-amino-1-(3-chloro-phenylethynyl)-cyclohexanol was obtained.

Following the same procedure, the following compounds can be obtained:

EXAMPLE 1.1

Furan-3-carboxylic acid [(1S,3S)-3-(3-chloro-phenylethynyl)-3-hydroxy-cyclohexyl]-amide $[\alpha]_D$=−94.3° (c=0.5, MeOH) MS (LC/MS): 344.2 [M+H]

EXAMPLE 1.2

Furan-2-carboxylic acid [(1R,3R)-3-(3-chloro-phenylethynyl)-3-hydroxy-cyclohexyl]-amide $[\alpha]_D$=+55.4° (c=0.5, MeOH) MS (LC/MS): 344.4 [M+H]

EXAMPLE 1.3

Furan-2-carboxylic acid [(1S,3S)-3-(3-chloro-phenylethynyl)-3-hydroxy-cyclohexyl]-amide $[\alpha]_D$=−58.8° (c=0.45, MeOH) MS (LC/MS): 344.4 [M+H]

EXAMPLE 1.4

3H-Imidazole-4-carboxylic acid [(1R,3R)-3-(3-chloro-phenylethynyl)-3-hydroxy-cyclohexyl]-amide $[\alpha]_D$=+72.0° (c=0.25, MeOH) MS (LC/MS): 344.5 [M+H]

EXAMPLE 1.5

3H-Imidazole-4-carboxylic acid [(1S,3S)-3-(3-chloro-phenylethynyl)-3-hydroxy-cyclohexyl]-amide $[\alpha]_D$=−83.8° (c=0.27, MeOH) MS (LC/MS): 334.5 [M+H]

EXAMPLE 1.6

4H-[1,2,4]Triazole-3-carboxylic acid [(1R,3R)-3-(3-chloro-phenylethynyl)-3-hydroxy-cyclohexyl]-amide $[\alpha]_D$=+84.5° (c=0.25, MeOH) MS (LC/MS): 345.4 [M+H]

EXAMPLE 1.7

4H-[1,2,4]Triazole-3-carboxylic acid [(1S,3S)-3-(3-chloro-phenylethynyl)-3-hydroxy-cyclohexyl]-amide $[\alpha]_D$=−92.3° (c=0.25, MeOH) MS (LC/MS): 345.4 [M+H]

EXAMPLE 1.8

2-Methyl-furan-3-carboxylic acid [(±)-(1R,3R)-3-(3-chloro-phenylethynyl)-3-hydroxy-cyclohexyl]-amide MS (LC/MS): 358.4 [M+H]TLC Rf: 0.55 (EtOAc/cyclohexane 1:1)

EXAMPLE 1.9

N-[(±)-(1R,3R)-3-(3-Chloro-phenylethynyl)-3-hydroxy-cyclohexyl]-3,4-difluoro-benzamide MS (LC/MS): 390.4 [M+H]TLC Rf: 0.45 (EtOAc/cyclohexane 1:1)

EXAMPLE 1.10

Benzo[1,3]dioxole-2-carboxylic acid [(±)-(1R,3R)-3-(3-chloro-phenylethynyl)-3-hydroxy-cyclohexyl]-amide MS (LC/MS): 398.4 [M+H]TLC Rf: 0.34 (EtOAc/cyclohexane 1:1)

EXAMPLE 1.11

5-Methyl-pyrazine-2-carboxylic acid [(±)-(1R,3R)-3-(3-chloro-phenylethynyl)-3-hydroxy-cyclohexyl]-amide MS (LC/MS): 370.6 [M+H]TLC Rf: 0.18 (EtOAc/cyclohexane 1:1)

EXAMPLE 1.12

Quinoxaline-2-carboxylic acid [(±)-(1R,3R)-3-(3-chloro-phenylethynyl)-3-hydroxy-cyclohexyl]-amide MS (LC/MS): 406.4 [M+H]TLC Rf: 0.22 (EtOAc/cyclohexane 1:1)

EXAMPLE 1.13

Benzofuran-2-carboxylic acid [(±)-(1R,3R)-3-(3-chloro-phenylethynyl)-3-hydroxy-cyclohexyl]-amide MS (LC/MS): 394.0 [M+H]TLC Rf: 0.37 (EtOAc/cyclohexane 1:1)

EXAMPLE 1.14

Benzooxazole-2-carboxylic acid [(±)-(1R,3R)-3-(3-chloro-phenylethynyl)-3-hydroxy-cyclohexyl]-amide MS (LC/MS): 395.3 [M+H]TLC Rf: 0.32 (EtOAc/cyclohexane 1:1)

EXAMPLE 1.15

2,5-Dimethyl-furan-3-carboxylic acid [(±)-(1R,3R)-3-(3-chloro-phenylethynyl)-3-hydroxy-cyclohexyl]-amide MS (LC/MS): 372.5 [M+H]TLC Rf: 0.58 (EtOAc/cyclohexane 1:1)

EXAMPLE 1.16

(R,S)-Tetrahydro-furan-3-carboxylic acid [(±)-(1R,3R)-3-(3-chloro-phenylethynyl)-3-hydroxy-cyclohexyl]-amide MS (LC/MS): 348.3 [M+H]TLC Rf: 0.24 (EtOAc/cyclohexane 1:1)

EXAMPLE 1.17

Furan-3-carboxylic acid ((1R,3R)-3-hydroxy-3-m-tolylethynyl-cyclohexyl)-amide $[\alpha]_D$=+99.9° (c=1, MeOH) MS (LC/MS): 324.2 [M+H]

EXAMPLE 1.18

Furan-3-carboxylic acid ((1S,3S)-3-hydroxy-3-m-tolylethynyl-cyclohexyl)-amide $[\alpha]_D$=−101.5° (c=1, MeOH) MS (LC/MS): 324.2 [M+H]

EXAMPLE 1.19

Furan-3-carboxylic acid ((±)-(1R,3R)-3-hydroxy-3-m-tolylethynyl-cyclohexyl)-amide Mp: 135-138° C. MS (LC/MS): 324.3 [M+H]

EXAMPLE 1.20

Furan-2-carboxylic acid ((1R,3R)-3-hydroxy-3-m-tolylethynyl-cyclohexyl)-amide $[\alpha]_D$=+66.2° (c=1, MeOH) Mp: 139-142° C. MS (LC/MS): 324.3 [M+H]

EXAMPLE 1.21

Furan-2-carboxylic acid ((1S,3S)-3-hydroxy-3-m-tolylethynyl-cyclohexyl)-amide $[\alpha]_D$=−61.9° (c=1, MeOH) Mp: 139-140° C. MS (LC/MS): 324.3 [M+H]

EXAMPLE 1.22

Furan-2-carboxylic acid ((±)(1R,3R)-3-hydroxy-3-m-tolylethynyl-cyclohexyl amide

MS (LC/MS): 324.3 [M+H]TLC Rf: 0.58 (EtOAc/MeOH 9:1)

EXAMPLE 1.23

Isoxazole-5-carboxylic acid ((1R,3R)-3-hydroxy-3-m-tolylethynyl-cyclohexyl)-amide $[\alpha]_D$=+61.2° (c=1, MeOH) TLC Rf: 0.42 (EtOAc/cyclohexane 1:1)

EXAMPLE 1.24

Isoxazole-5-carboxylic acid ((1S,3S)-3-hydroxy-3-m-tolylethynyl-cyclohexyl)-amide $[\alpha]_D$=−64.4° (c=1, MeOH) TLC Rf: 0.42 (EtOAc/cyclohexane 1:1)

EXAMPLE 1.25

Isoxazole-5-carboxylic acid ((±)-(1R,3R)-3-hydroxy-3-m-tolylethynyl-cyclohexyl)-amide MS (LC/MS): 325.2 [M+H]TLC Rf: 0.42 (EtOAc/cyclohexane 1:1)

EXAMPLE 1.26

5-Methyl-pyrazine-2-carboxylic acid ((±)-(1R,3R)-3-hydroxy-3-m-tolylethynyl-cyclohexyl)-amide MS (LC/MS): 350.2 [M+H]TLC Rf: 0.54 (EtOAc/MeOH 9:1)

EXAMPLE 1.27

4H-[1,2,4]Triazole-3-carboxylic acid ((±)-(1R,3R)-3-hydroxy-3-m-tolylethynyl-cyclohexyl)-amide MS (LC/MS): 325.2 [M+H]TLC Rf: 0.42 (EtOAc)

EXAMPLE 1.28

3H-Imidazole-4-carboxylic acid ((±)-(1R,3R)-3-hydroxy-3-m-tolylethynyl-cyclohexyl)-amide MS (LC/MS): 324.2 [M+H]TLC Rf: 0.12 (EtOAc)

EXAMPLE 1.29

Tetrahydro-pyran-4-carboxylic acid ((±)-(1R,3R)-3-hydroxy-3-m-tolylethynyl-cyclohexyl)-amide MS (LC/MS): 342.2 [M+H]TLC Rf: 0.48 (EtOAc)

EXAMPLE 1.30

1-Methyl-1H-imidazole-4-carboxylic acid ((±)-(1R,3R)-3-hydroxy-3-m-tolylethynyl-cyclohexyl)amide MS (LC/MS): 338.4 [M+H]TLC Rf: 0.20 (EtOAc)

EXAMPLE 1.31

(R,S)-Tetrahydro-furan-2-carboxylic acid ((±)-(1R,3R)-3-hydroxy-3-m-tolylethynyl-cyclohexyl)amide MS (LC/MS): 328.4 [M+H]TLC Rf: 0.54 (EtOAc)

EXAMPLE 1.32

(R,S)-Tetrahydro-furan-3-carboxylic acid ((±)-(1R,3R)-3-hydroxy-3-m-tolylethynyl-cyclohexyl)-amide MS (LC/MS): 328.4 [M+H]TLC Rf: 0.55 (EtOAc)

EXAMPLE 1.33

Furan-3-carboxylic acid [(1R,3R)-3-(3-fluoro-phenylethynyl)-3-hydroxy-cyclohexyl]-amide $[\alpha]_D$=+96.1° (c=0.3, MeOH) MS (LC/MS): 328.1 [M+H]

EXAMPLE 1.34

Furan-3-carboxylic acid [(1S,3S)-3-(3-fluoro-phenylethynyl)-3-hydroxy-cyclohexyl]-amide $[\alpha]_D$=−89.9 (c=0.5, MeOH) MS (LC/MS): 328.2 [M+H]

EXAMPLE 1.35

Furan-2-carboxylic acid [(1R,3R)-3-(3-fluoro-phenylethynyl)-3-hydroxy-cyclohexyl]-amide $[\alpha]_D$=+65.5 (c=0.25, MeOH) MS (LC/MS): 328.2 [M+H]

EXAMPLE 1.36

Furan-2-carboxylic acid [(1S,3S)-3-(3-fluoro-phenylethynyl)-3-hydroxy-cyclohexyl]-amide $[\alpha]_D$=−61.5 (c=0.5, MeOH) MS (LC/MS): 328.2 [M+H]

EXAMPLE 1.37

3H-Imidazole-4-carboxylic acid [(±)-(1R,3R)-3-(3-fluoro-phenylethynyl)-3-hydroxy-cyclohexyl]-amide Mp: 190-191° C. MS (LC/MS): 328.2 [M+H]

EXAMPLE 1.38

N-[(1S,3S)-3-(3-Chloro-phenylethynyl)-3-hydroxy-cyclohexyl]-3,4-difluoro-benzamide $[\alpha]_D$=−68.7 (c=2.5, MeOH) MS (LC/MS): 392.1 [M+H]

EXAMPLE 1.39

N-[(1R,3R)-3-(3-Chloro-phenylethynyl)-3-hydroxy-cyclohexyl]-3,4-difluoro-benzamide $[\alpha]_D$=+68.9 (c=1.5, MeOH) MS (LC/MS): 392.1 [M+H]

EXAMPLE 1.40

Pyridine-2-carboxylic acid [(1S,3S)-3-(3-chloro-phenylethynyl)-3-hydroxy-cyclohexyl]-amide $[\alpha]_D$=−62.6 (c=0.5, MeOH) MS (LC/MS): 355.1 [M+H]

EXAMPLE 1.41

Pyridine-2-carboxylic acid [(1R,3R)-3-(3-chloro-phenylethynyl)-3-hydroxy-cyclohexyl]-amide $[\alpha]_D$=+53.1 (c=1.7, MeOH) MS (LC/MS): 355.1 [M+H]

EXAMPLE 1.42

N-[(1S,3S)-3-(3-Chloro-phenylethynyl)-3-hydroxy-cyclohexyl]-nicotinamide $[\alpha]_D$=−69.4 (c=0.7, MeOH) MS (LC/MS): 355.1 [M+H]

EXAMPLE 1.43

N-[(1R,3R)-3-(3-Chloro-phenylethynyl)-3-hydroxy-cyclohexyl]-nicotinamide $[\alpha]_D$=+70.2 (c=0.5, MeOH) MS (LC/MS): 355.1 [M+H]

EXAMPLE 1.44

Benzo[1,3]dioxole-2-carboxylic acid [(1S,3S)-3-(3-chloro-phenylethynyl)-3-hydroxy-cyclohexyl]-amide $[\alpha]_D$=−83.8° (1% EtOH) MS (LC/MS): 420 [M+Na]

EXAMPLE 1.45

5-Methyl-pyrazine-2-carboxylic acid [(1S,3S)-3-(3-chloro-phenylethynyl)-3-hydroxy-cyclohexyl]-amide $[\alpha]_D$=−34.5° (1% EtOH) MS (LC/MS): 370 [M+H]

EXAMPLE 1.46

2-Methyl-furan-3-carboxylic acid [(1S,3S)-3-(3-chloro-phenylethynyl)-3-hydroxy-cyclohexyl]-amide $[\alpha]_D$=−780.3° (1% EtOH) MS (LC/MS): 380 [M+Na]

EXAMPLE 1.47

(R)-Tetrahydro-furan-2-carboxylic acid [(1R,3R)-3-(3-chloro-phenylethynyl)-3-hydroxy-cyclohexyl]-amide $[\alpha]_D$=+56.4 (c=0.5, MeOH) MS (LC/MS): 348 [M+H]

EXAMPLE 1.48

(S)-Tetrahydro-furan-2-carboxylic acid [(1R,3R)-3-(3-chloro-phenylethynyl)-3-hydroxy-cyclohexyl]-amide $[\alpha]_D$=+66.8 (c=0.5, MeOH) MS (LC/MS): 348 [M+H]

EXAMPLE 1.49

Isoxazole-5-carboxylic acid [(1S,3S)-3-(3-chloro-phenylethynyl)-3-hydroxy-cyclohexyl]-amide $[\alpha]_D$=−76.9° (1% EtOH) MS (LC/MS): 367 [M+Na]

EXAMPLE 1.50

5-Methyl-pyrazine-2-carboxylic acid [(1R,3R)-3-(3-chloro-phenylethynyl)-3-hydroxy-cyclohexyl]-amide $[\alpha]_D$=+7.3° (1% EtOH) MS (LC/MS): 392 [M+Na]

EXAMPLE 1.51

2-Methyl-furan-3-carboxylic acid [(1R,3R)-3-(3-chloro-phenylethynyl)-3-hydroxy-cyclohexyl]-amide $[\alpha]_D$=+119.6° (1% EtOH) MS (LC/MS): 380 [M+Na]

EXAMPLE 1.52

Isoxazole-5-carboxylic acid [(1R,3R)-3-(3-chloro-phenylethynyl)-3-hydroxy-cyclohexyl]-amide $[\alpha]_D$=+95.70 (1% EtOH) MS (LC/MS): 367 [M+Na]

EXAMPLE 1.53

5-Chloro-furan-2-carboxylic acid [(1R,3R)-3-(3-chloro-phenylethynyl)-3-hydroxy-cyclohexyl]-amide $[\alpha]_D$=+18.54 (c=0.6, MeOH) MS (LC/MS): 379.1 [M+H]

EXAMPLE 1.54

5-Chloro-furan-2-carboxylic acid [(1S,3S)-3-(3-chloro-phenylethynyl)-3-hydroxy-cyclohexyl]-amide $[\alpha]_D$=−18.9 (c=0.7, MeOH) MS (LC/MS): 379.1 [M+H]

EXAMPLE 1.55

(S)-Tetrahydro-furan-3-carboxylic acid [(1R,3R)-3-(3-chloro-phenylethynyl)-3-hydroxy-cyclohexyl]-amide MS (LC/MS): 348 [M+H] TLC Rf: 0.10 (EtOAc/cyclohexane 2:1)

EXAMPLE 1.56

(R)-Tetrahydro-furan-3-carboxylic acid [(1R,3R)-3-(3-chloro-phenylethynyl)-3-hydroxy-cyclohexyl]-amide MS (LC/MS): 348 [M+H] TLC Rf: 0.10 (EtOAc/cyclohexane 2:1)

EXAMPLE 1.57

N-[(1S,3S)-3-(3-Chloro-phenylethynyl)-3-hydroxy-cyclohexyl]-isonicotinamide $[\alpha]_D$=−83.11° (c=0.8, MeOH) MS (LC/MS): 355.1 [M+H]

EXAMPLE 1.58

N-[(1R,3R)-3-(3-Chloro-phenylethynyl)-3-hydroxy-cyclohexyl]-isonicotinamide $[\alpha]_D$=39.14° (c=0.7, MeOH) MS (LC/MS): 355.1 [M+H]

EXAMPLE 1.59

3,5-Difluoro-pyridine-2-carboxylic acid [(1R,3R)-3-(3-chloro-phenylethynyl)-3-hydroxy-cyclohexyl]-amide $[\alpha]_D$=60.2° (c=0.85, MeOH) MS (LC/MS): 391.3 [M+H]

EXAMPLE 1.60

3,5-Difluoro-pyridine-2-carboxylic acid [(1S,3S)-3-(3-chloro-phenylethynyl)-3-hydroxy-cyclohexyl]-amide $[\alpha]_D$=−59.25° (c=0.94, MeOH) MS (LC/MS): 391.3 [M+H]

EXAMPLE 1.61

6-Methyl-pyridine-2-carboxylic acid [(1S,3S)-3-(3-chloro-phenylethynyl)-3-hydroxy-cyclohexyl]-amide $[\alpha]_D$=−25.67° (c=0.63, MeOH) MS (LC/MS): 369.1 [M+H]

EXAMPLE 1.62

6-Methyl-pyridine-2-carboxylic acid [(1R,3R)-3-(3-chloro-phenylethynyl)-3-hydroxy-cyclohexyl]-amide $[\alpha]_D$=30.20 (c=1, MeOH) MS (LC/MS): 369.1 [M+H]

EXAMPLE 1.63

5-Chloro-pyridine-2-carboxylic acid [(1R,3R)-3-(3-chloro-phenylethynyl)-3-hydroxy-cyclohexyl]-amide $[\alpha]_D$=32.26° (c=0.68, MeOH) MS (LC/MS): 390.3 [M+H]

EXAMPLE 1.64

5-Chloro-pyridine-2-carboxylic acid [(1S,3S)-3-(3-chloro-phenylethynyl)-3-hydroxy-cyclohexyl]-amide $[\alpha]_D$=−30.27° (c=0.74, MeOH) MS (LC/MS): 390.3 [M+H]

EXAMPLE 1.65

6-Chloro-pyridine-2-carboxylic acid [(1R,3R)-3-(3-chloro-phenylethynyl)-3-hydroxy-cyclohexyl]-amide $[\alpha]_D$=12.6° (c=0.5, MeOH) MS (LC/MS): 390.3 [M+H]

EXAMPLE 1.66

6-Chloro-pyridine-2-carboxylic acid [(1S,3S)-3-(3-chloro-phenylethynyl)-3-hydroxy-cyclohexyl]-amide $[\alpha]_D$=−9.33° (c=0.45, MeOH) MS (LC/MS): 390.3 [M+H]

EXAMPLE 1.67

5-Chloro-1-methyl-1H-pyrrole-2-carboxylic acid [(1R,3R)-3-(3-chloro-phenylethynyl)-3-hydroxy-cyclohexyl]-amide $[\alpha]_D$=87.2° (c=0.66, MeOH) MS (LC/MS): 392.3 [M+H]

EXAMPLE 1.68

5-Chloro-1-methyl-1H-pyrrole-2-carboxylic acid [(1S,3S)-3-(3-chloro-phenylethynyl)-3-hydroxy-cyclohexyl]-amide $[\alpha]_D$=−97° (c=0.65, MeOH) MS (LC/MS): 392.3 [M+H]

EXAMPLE 1.69

5-Chloro-1H-pyrrole-2-carboxylic acid [(1R,3R)-3-(3-chloro-phenylethynyl)-3-hydroxy-cyclohexyl]-amide $[\alpha]_D$=83.1° (c=0.58, MeOH) MS (LC/MS): 378.3 [M+H]

EXAMPLE 1.70

5-Chloro-1H-pyrrole-2-carboxylic acid [(1S,3S)-3-(3-chloro-phenylethynyl)-3-hydroxy-cyclohexyl]-amide $[\alpha]_D$=−79.32° (c=0.58, MeOH) MS (LC/MS): 378.3 [M+H]

EXAMPLE 1.71

N-[(1S,3S)-3-(3-Chloro-phenylethynyl)-3-hydroxy-cyclohexyl]-4-dimethyl amino-benzamide MS (LC/MS): 397 [M+H]TLC Rf: 0.33 (EtOAc/hexane 1:1)

EXAMPLE 1.72

1H-Pyrrole-3-carboxylic acid [(1S,3S)-3-(3-chloro-phenylethynyl)-3-hydroxy-cyclohexyl]-amide MS (LC/MS): 365 [M+Na]TLC Rf: 0.10 (EtOAc/hexane 1:1)

EXAMPLE 1.73

N-[(1S,3S)-3-(3-chloro-phenylethynyl)-3-hydroxy-cyclohexyl]-4-methyl-benzamide

A solution of TBTU (2-(1H-benzotriazole-1-yl)-1,1,3,3-tetramethyluronium tetrafluoroborate)(29.9 mg, 0.093 mmol) in DMA (0.23 ml) and DIPEA (36 µl, 0.213 mmol) was added to solid 4-methylbenzoic acid (11.6 mg, 0.085 mmol) under argon atmosphere at room temperature. After stirring for 20 min., a solution of (1S,3S)-3-amino-1-(3-chloro-phenylethynyl)-cyclohexanol (21.2 mg, 0.085 mmol) in DMA (0.43 ml) was added and the crude reaction mixture was purified without further treatment after stirring for 24 h on a preparative LC/MS system, yielding the title compound (25.1 mg, 0.068 mmol).

MS (LC/MS): 368 [M+H]HPLC Rt: 7.01 min (gradient elution)

General LC/MS purification conditions: The crude reaction mixture was injected onto a Waters Atlantis C-18 column (dimensions: 19×100 mm, particle size: 5 µm, pore size: 100 A) and eluted using a 15 ml/min gradient flow rate. The gradient used is as following:

0 min: water containing 0.1% TFA (95%), acetonitrile (5%)
1 min: water containing 0.1% TFA (95%), acetonitrile (5%)
7 min: water containing 0.1% TFA (5%), acetonitrile (95%)
9 min: water containing 0.1% TFA (5%), acetonitrile (95%)

Fractions were triggered by MS detection (ES+ mode) of the expected molecular ion peak and UV absorption was measured at 254 nm. The recorded data was processed using the MassLynx 4.0 program from Waters.

Following the same procedure, the following compounds can be obtained:

EXAMPLE 1.74

N-[(1S,3S)-3-(3-Chloro-phenylethynyl)-3-hydroxy-cyclohexyl]-4-methyl-benzamide

MS (LC/MS): 368 [M+H]HPLC Rt: 7.01 min (gradient elution)

EXAMPLE 1.75

N-[(1S,3S)-3-(3-Chloro-phenylethynyl)-3-hydroxy-cyclohexyl]-3-fluoro-benzamide

MS (LC/MS): 372 [M+H]HPLC Rt: 6.68 min (gradient elution)

EXAMPLE 1.76

N-[(1S,3S)-3-(3-Chloro-phenylethynyl)-3-hydroxy-cyclohexyl]-2-ethyl-butyramide

MS (LC/MS): 348 [M+H]HPLC Rt: 6.82 min (gradient elution)

EXAMPLE 1.77

N-[(1S,3S)-3-(3-Chloro-phenylethynyl)-3-hydroxy-cyclohexyl]-4-(2,5-dimethoxy-phenyl)-4-oxo-butyramide MS (LC/MS): 470 [M+H]HPLC Rt: 6.68 min (gradient elution)

EXAMPLE 1.78

2-(2-Benzyloxy-ethoxy)-N-[(1S,3S)-3-(3-chloro-phenylethynyl)-3-hydroxy-cyclohexyl]-acetamide MS (LC/MS): 442 [M+H]HPLC Rt: 6.97 min (gradient elution)

EXAMPLE 1.79

N-[(1S,3S)-3-(3-Chloro-phenylethynyl)-3-hydroxy-cyclohexyl]-2-phenyl-acetamide

MS (LC/MS): 368 [M+H]HPLC Rt: 6.64 min (gradient elution)

EXAMPLE 180

N-[(1S,3S)-3-(3-Chloro-phenylethynyl)-3-hydroxy-cyclohexyl]-3-(1H-indol-4-yl)-propionamide MS (LC/MS): 421 [M+H]HPLC Rt: 6.46 min (gradient elution)

EXAMPLE 1.81

2-Benzo[1,3]dioxol-5-yl-N-[(1S,3S)-3-(3-chloro-phenylethynyl)-3-hydroxy-cyclohexyl]-acetamide MS (LC/MS): 412 [M+H]HPLC Rt: 6.56 min (gradient elution)

EXAMPLE 1.82

N-[(1S,3S)-3-(3-Chloro-phenylethynyl)-3-hydroxy-cyclohexyl]-2-phenoxy-propionamide MS (LC/MS): 398 [M+H]HPLC Rt: 6.97 min (gradient elution)

EXAMPLE 1.83

N-[(1S,3S)-3-(3-Chloro-phenylethynyl)-3-hydroxy-cyclohexyl]-2-(2-fluoro-phenyl)acetamide MS (LC/MS): 386 [M+H]HPLC Rt: 6.69 min (gradient elution)

EXAMPLE 1.84

5-Hydroxy-1H-indole-2-carboxylic acid [(1S,3S)-3-(3-chloro-phenylethynyl)-3-hydroxy-cyclohexyl]-amide MS (LC/MS): 409 [M+H]HPLC Rt: 6.06 min (gradient elution)

EXAMPLE 1.85

1-Methyl-1H-pyrrole-2-carboxylic acid [(1S,3S)-3-(3-chloro-phenylethynyl)-3-hydroxy-cyclohexyl]-amide MS (LC/MS): 357 [M+H]HPLC Rt: 6.62 min (gradient elution)

EXAMPLE 1.86

N-[(1S,3S)-3-(3-Chloro-phenylethynyl)-3-hydroxy-cyclohexyl]-terephthalamic acid methyl ester MS (LC/MS): 412 [M+H]HPLC Rt: 6.62 min (gradient elution)

EXAMPLE 1.87

N-[(1S,3S)-3-(3-Chloro-phenylethynyl)-3-hydroxy-cyclohexyl]-2-(2-trifluoromethoxy-phenyl)acetamide MS (LC/MS): 452 [M+H]HPLC Rt: 7.04 min (gradient elution)

EXAMPLE 1.88

5-Chloro-N-[(1S,3S)-3-(3-chloro-phenylethynyl)-3-hydroxy-cyclohexyl]-2-hydroxy-benzamide MS (LC/MS): 404 [M+H]HPLC Rt: 7.34 min (gradient elution)

EXAMPLE 1.89

N-[(1S,3S)-3-(3-Chloro-phenylethynyl)-3-hydroxy-cyclohexyl]-4-hydroxy-benzamide

MS (LC/MS): 370 [M+H]HPLC Rt: 5.95 min (gradient elution)

EXAMPLE 1.90

N-[(1S,3S)-3-(3-Chloro-phenylethynyl)-3-hydroxy-cyclohexyl]-2-hydroxy-benzamide

MS (LC/MS): 370 [M+H]HPLC Rt: 6.97 min (gradient elution)

EXAMPLE 1.91

4-Amino-N-[(1S,3S)-3-(3-chloro-phenylethynyl)-3-hydroxy-cyclohexyl]-benzamide

MS (LC/MS): 369 [M+H]HPLC Rt: 5.36 min (gradient elution)

EXAMPLE 1.92

4-Amino-5-chloro-N-[(1S,3S)-3-(3-chloro-phenylethynyl)-3-hydroxy-cyclohexyl]-2-methoxy-benzamide MS (LC/MS): 433 [M+H]HPLC Rt: 6.60 min (gradient elution)

EXAMPLE 1.93

3-Amino-4-chloro-N-[(1S,3S)-3-(3-chloro-phenylethynyl)-3-hydroxy-cyclohexyl]-benzamide MS (LC/MS): 403 [M+H]HPLC Rt: 6.51 min (gradient elution)

EXAMPLE 1.94

3-Amino-N-[(1S,3S)-3-(3-chloro-phenylethynyl)-3-hydroxy-cyclohexyl]-4-methyl-benzamide MS (LC/MS): 383 [M+H]HPLC Rt: 5.16 min (gradient elution)

EXAMPLE 1.95

2-Amino-N-[(1S,3S)-3-(3-chloro-phenylethynyl)-3-hydroxy-cyclohexyl]-nicotinamide MS (LC/MS): 370 [M+H]HPLC Rt: 4.84 min (gradient elution)

EXAMPLE 1.96

N-[(1S,3S)-3-(3-Chloro-phenylethynyl)-3-hydroxy-cyclohexyl]-4-hydroxy-3-methoxy-benzamide MS (LC/MS): 400 [M+H]HPLC Rt: 5.95 min (gradient elution)

EXAMPLE 1.97

N-[(1S,3S)-3-(3-Chloro-phenylethynyl)-3-hydroxy-cyclohexyl]-2-fluoro-benzamide

MS (LC/MS): 372 [M+H]HPLC Rt: 6.75 min (gradient elution)

EXAMPLE 1.98

N-[(1S,3S)-3-(3-Chloro-phenylethynyl)-3-hydroxy-cyclohexyl]-4-methanesulfonyl-benzamide MS (LC/MS): 432 [M+H]HPLC Rt: 6.05 min (gradient elution)

EXAMPLE 1.99

Pyridine-2-carboxylic acid [(1S,3S)-3-(3-chloro-phenylethynyl)-3-hydroxy-cyclohexyl]-amide MS (LC/MS): 355 [M+H]HPLC Rt: 6.52 min (gradient elution)

EXAMPLE 1.100

3-Amino-pyrazine-2-carboxylic acid [(1S,3S)-3-(3-chloro-phenylethynyl)-3-hydroxy-cyclohexyl]-amide MS (LC/MS): 371 [M+H]HPLC Rt: 6.45 min (gradient elution)

EXAMPLE 1.101

6-Amino-N-[(1S,3S)-3-(3-chloro-phenylethynyl)-3-hydroxy-cyclohexyl]-nicotinamide MS (LC/MS): 370 [M+H]HPLC Rt: 4.77 min (gradient elution)

EXAMPLE 1.102

4-(4-Amino-benzoylamino)-benzoic acid [(1R,3R)-3-(3-chloro-phenylethynyl)-3-hydroxy-cyclohexyl]-amide MS (LC/MS): 488 [M+H]HPLC Rt: 5.67 min (gradient elution)

EXAMPLE 1.103

2,6-Dioxo-1,2,3,6-tetrahydro-pyrimidine-4-carboxylic acid [(1S,3S)-3-(3-chloro-phenylethynyl)-3-hydroxy-cyclohexyl]-amide MS (LC/MS): 388 [M+H]HPLC Rt: 5.34 min (gradient elution)

EXAMPLE 1.104

N-[(1S,3S)-3-(3-Chloro-phenylethynyl)-3-hydroxy-cyclohexyl]-isonicotinamide

MS (LC/MS): 355 [M+H]HPLC Rt: 4.79 min (gradient elution)

EXAMPLE 1.105

3-Chloro-N-[(1S,3S)-3-(3-chloro-phenylethynyl)-3-hydroxy-cyclohexyl]-benzamide

MS (LC/MS): 388 [M+H]HPLC Rt: 7.08 min (gradient elution)

EXAMPLE 1.106

N-[(1S,3S)-3-(3-Chloro-phenylethynyl)-3-hydroxy-cyclohexyl]-2,3-dimethoxy-benzamide MS (LC/MS): 414 [M+H]HPLC Rt: 6.97 min (gradient elution)

EXAMPLE 1.107

N-[(1S,3S)-3-(3-Chloro-phenylethynyl)-3-hydroxy-cyclohexyl]-4-oxo-4-phenyl-butyramide MS (LC/MS): 410 [M+H]HPLC Rt: 6.65 min (gradient elution)

EXAMPLE 1.108

2-Chloro-N-[(1S,3S)-3-(3-chloro-phenylethynyl)-3-hydroxy-cyclohexyl]-nicotinamide MS (LC/MS): 389 [M+H]HPLC Rt: 6.21 min (gradient elution)

EXAMPLE 1.109

5-Bromo-N-[(1S,3S)-3-(3-chloro-phenylethynyl)-3-hydroxy-cyclohexyl]-nicotinamide MS (LC/MS): 433 [M+H]HPLC Rt: 6.58 min (gradient elution)

EXAMPLE 1.110

Isoquinoline-1-carboxylic acid [(1S,3S)-3-(3-chloro-phenylethynyl)-3-hydroxy-cyclohexyl]-amide MS (LC/MS): 405 [M+H]HPLC Rt: 6.97 min (gradient elution)

EXAMPLE 1.111

Pyrazine-2-carboxylic acid [(1S,3S)-3-(3-chloro-phenylethynyl)-3-hydroxy-cyclohexyl]-amide MS (LC/MS): 356 [M+H]HPLC Rt: 6.17 min (gradient elution)

EXAMPLE 1.112

3-Benzoyl-pyridine-2-carboxylic acid [(1S,3S)-3-(3-chloro-phenylethynyl)-3-hydroxy-cyclohexyl]-amide MS (LC/MS): 459 [M+H]HPLC Rt: 6.54 min and 7.10 min (gradient elution)

EXAMPLE 1.113

N-[(1S,3S)-3-(3-Chloro-phenylethynyl)-3-hydroxy-cyclohexyl]-2-methyl-nicotinamide MS (LC/MS): 369 [M+H]HPLC Rt: 4.73 min (gradient elution)

EXAMPLE 1.114

Quinoxaline-2-carboxylic acid [(1S,3S)-3-(3-chloro-phenylethynyl)-3-hydroxy-cyclohexyl]-amide MS (LC/MS): 406 [M+H]HPLC Rt: 6.95 min (gradient elution)

EXAMPLE 1.115

Pyridazine-4-carboxylic acid [(1S,3S)-3-(3-chloro-phenylethynyl)-3-hydroxy-cyclohexyl]-amide MS (LC/MS): 356 [M+H]HPLC Rt: 5.60 min (gradient elution)

EXAMPLE 1.116

N-[(1S,3S)-3-(3-Chloro-phenylethynyl)-3-hydroxy-cyclohexyl]-2-methylsulfanyl-nicotinamide MS (LC/MS): 401 [M+H]HPLC Rt: 6.47 min (gradient elution)

EXAMPLE 1.117

N-[(1S,3S)-3-(3-Chloro-phenylethynyl)-3-hydroxy-cyclohexyl]-4-trifluoromethyl-nicotinamide MS (LC/MS): 423 [M+H]HPLC Rt: 6.28 min (gradient elution)

EXAMPLE 1.118

2-Chloro-N-[(1S,3S)-3-(3-chloro-phenylethynyl)-3-hydroxy-cyclohexyl]-isonicotinamide MS (LC/MS): 389 [M+H]HPLC Rt: 6.49 min (gradient elution)

EXAMPLE 1.119

2-Chloro-N-[(1S,3S)-3-(3-chloro-phenylethynyl)-3-hydroxy-cyclohexyl]-6-methyl-nicotinamide MS (LC/MS): 403 [M+H]HPLC Rt: 6.34 min (gradient elution)

EXAMPLE 1.120

6-Chloro-N-[(1S,3S)-3-(3-chloro-phenylethynyl)-3-hydroxy-cyclohexyl]-nicotinamide MS (LC/MS): 389 [M+H]HPLC Rt: 6.45 min (gradient elution)

EXAMPLE 1.121

2-Chloro-N-[(1S,3S)-3-(3-chloro-phenylethynyl)-3-hydroxy-cyclohexyl]-6-methyl-isonicotinamide MS (LC/MS): 403 [M+H]HPLC Rt: 6.69 min (gradient elution)

EXAMPLE 1.122

N-[(1S,3S)-3-(3-Chloro-phenylethynyl)-3-hydroxy-cyclohexyl]-2-(4,5-dimethoxy-3-oxo-1,3-dihydro-isobenzofuran-1-yl)-acetamide MS (LC/MS): 484 [M+H]HPLC Rt: 6.17 min (gradient elution)

EXAMPLE 1.123

1,4,5,6-Tetrahydro-cyclopentapyrazole-3-carboxylic acid [(1S,3S)-3-(3-chloro-phenylethynyl)-3-hydroxy-cyclohexyl]-amide MS (LC/MS): 384 [M+H]HPLC Rt: 6.10 min (gradient elution)

EXAMPLE 1.124

N-[(1S,3S)-3-(3-Chloro-phenylethynyl)-3-hydroxy-cyclohexyl]-3-(1H-indol-2-yl)-propionamide MS (LC/MS): 421 [M+H]HPLC Rt: 6.59 min (gradient elution)

EXAMPLE 1.125

6-[(1S,3S)-3-(3-Chloro-phenylethynyl)-3-hydroxy-cyclohexylcarbamoyl]-pyridine-2-carboxylic acid isopropyl ester MS (LC/MS): 441 [M+H]HPLC Rt: 6.97 min (gradient elution)

EXAMPLE 1.126

Quinoline-6-carboxylic acid [(1S,3S)-3-(3-chloro-phenylethynyl)-3-hydroxy-cyclohexyl]-amide MS (LC/MS): 405 [M+H]HPLC Rt: 4.95 min (gradient elution)

EXAMPLE 1.127

5-Methyl-isoxazole-4-carboxylic acid [(1S,3S)-3-(3-chloro-phenylethynyl)-3-hydroxy-cyclohexyl]-amide MS (LC/MS): 359 [M+H]HPLC Rt: 6.23 min (gradient elution)

EXAMPLE 1.128

Benzofuran-3-carboxylic acid [(1S,3S)-3-(3-chloro-phenylethynyl)-3-hydroxy-cyclohexyl]-amide MS (LC/MS): 394 [M+H]HPLC Rt: 7.01 min (gradient elution)

EXAMPLE 1.129

N-[(1S,3S)-3-(3-Chloro-phenylethynyl)-3-hydroxy-cyclohexyl]-2-(2-methoxy-phenoxy)-acetamide MS (LC/MS): 414 [M+H]HPLC Rt: 6.76 min (gradient elution)

What is claimed is:

1. A process for the preparation of a compound of formula (I)

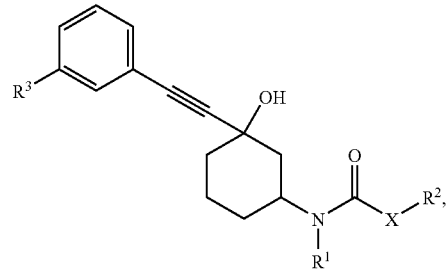

wherein
$R^1$ represents hydrogen or alkyl;
$R^2$ represents an unsubstituted or substituted heterocycle, or
$R^2$ represents an unsubstituted or substituted aryl;
$R^3$ represents alkyl or halogen;
X represents a single bond or an alkandiyl-group, optionally interrupted by one or more oxygen atoms or carbonyl groups or carbonyloxy groups;
in free base or acid addition salt form, comprising:
reacting a compound of formula (II)

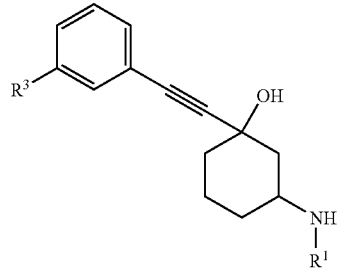

with a compound of formula (III)

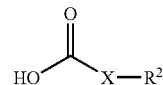

and recovering the resulting compound of formula (I) in free base or acid addition salt form.

2. A compound of formula (I)

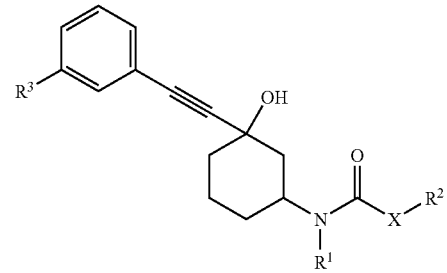

wherein:
$R^1$ represents hydrogen or $C_{1-12}$alkyl;

R² represents an unsubstituted, or a single or twofold substituted, heterocycle selected from the group consisting of wherein the substituents of the substituted heterocycle are selected from the group consisting of fluoro, chloro, methyl, methylthio and amino;
R³ represents $C_{1-12}$alkyl or halogen; and
X represents a single bond;
in free base or acid addition salt form.

3. The compound of formula (I) according to claim 2, wherein
R¹ hydrogen;
R² represents an unsubstituted, or a single or twofold substituted, heterocycle of the formula wherein the substituents of the substituted heterocycle are selected from the group consisting of fluoro, chloro and methyl; and
R³ represents chloro.

4. The compound of formula (I) according to claim 2, wherein
R¹ represents hydrogen;
R² represents an unsubstituted, or a single or twofold substituted, heterocycle of the formula wherein the substituents of the substituted heterocycle are selected from the group consisting of fluoro, chloro and methyl; and
R³ represents chloro.

5. The trans-isomer of a compound of formula (I) according to claim 2.

6. Furan-2-carboxylic acid [(1R,3R)-3-(3-chloro-phenylethynyl)-3-hydroxy-cyclohexyl]-amide in free base or acid addition salt form.

7. Furan-2-carboxylic acid [(1S,3S)-3-(3-chloro-phenylethynyl)-3-hydroxy-cyclohexyl]-amide in free base or acid addition salt form.

8. 5-Chloro-furan-2-carboxylic acid [(1R,3R)-3-(3-chloro-phenylethynyl)-3-hydroxy-cyclohexyl]-amide in free base or acid addition salt form.

9. 5-Chloro-furan-2-carboxylic acid [(1S,3S)-3-(3-chloro-phenylethynyl)-3-hydroxy-cyclohexyl]-amide in free base or acid addition salt form.

10. A compound selected from the group consisting of:
N-[(1S,3S)-3-(3-Chloro-phenylethynyl)-3-hydroxy-cyclohexyl]-nicotinamide;
N-[(1R,3R)-3-(3-Chloro-phenylethynyl)-3-hydroxy-cyclohexyl]-nicotinamide;
2-Amino-N-[(1S,3S)-3-(3-chloro-phenylethynyl)-3-hydroxy-cyclohexyl]-nicotinamide;
6-Amino-N-[(1S,3S)-3-(3-chloro-phenylethynyl)-3-hydroxy-cyclohexyl]-nicotinamide;
2-Chloro-N-[(1S,3S)-3-(3-chloro-phenylethynyl)-3-hydroxy-cyclohexyl]-nicotinamide;
5-Bromo-N-[(1S,3S)-3-(3-chloro-phenylethynyl)-3-hydroxy-cyclohexyl]-nicotinamide;
N-[(1S,3S)-3-(3-Chloro-phenylethynyl)-3-hydroxy-cyclohexyl]-2-methyl-nicotinamide;
N-[(1S,3S)-3-(3-Chloro-phenylethynyl)-3-hydroxy-cyclohexyl]-2-methylsulfanyl-nicotinamide;
N-[(1S,3S)-3-(3-Chloro-phenylethynyl)-3-hydroxy-cyclohexyl]-4-trifluoromethyl-nicotinamide;
2-Chloro-N-[(1S,3S)-3-(3-chloro-phenylethynyl)-3-hydroxy-cyclohexyl]-6-methyl-nicotinamide; and
6-Chloro-N-[(1S,3S)-3-(3-chloro-phenylethynyl)-3-hydroxy-cyclohexyl]-nicotinamide; in free base or acid addition salt form.

11. N-[(1R,3R)-3-(3-Chloro-phenylethynyl)-3-hydroxy-cyclohexyl]-nicotinamide in free base or acid addition salt form.

12. N-[(1S,3S)-3-(3-Chloro-phenylethynyl)-3-hydroxy-cyclohexyl]-nicotinamide in free base or acid addition salt form.

13. A pharmaceutical composition comprising a compound of any one of claims 2 to 12 in free base or pharmaceutically acceptable acid addition salt form, in association with a pharmaceutical carrier or diluent.

14. A process for the preparation of a compound of formula (I)

(I)

wherein:
R¹ represents hydrogen or $C_{1-12}$alkyl;
R² represents an unsubstituted, or a single or twofold substituted, heterocycle selected from the group consisting of wherein the substituents of the substituted heterocycle are selected from the group consisting of fluoro, chioro, methyl, methylthio and amino;
R³ represents $C_{1-12}$alkyl or halogen; and
X represents a single bond;

in free base or acid addition salt form, comprising:
reacting a compound of formula (II)
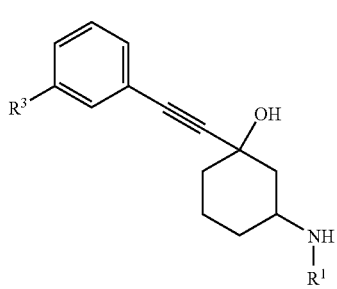
(II)
with a compound of formula (III)
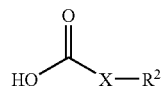
(III)
and recovering the resulting compound of formula (I) in free base or acid addition salt form.
* * * * *